United States Patent
Bocquillon et al.

(10) Patent No.: US 7,483,794 B2
(45) Date of Patent: Jan. 27, 2009

(54) METHOD FOR PREDICTING THE WEAR OF A TIRE AND SYSTEM FOR IMPLEMENTING IT

(75) Inventors: Arnaud Bocquillon, Clermont-Ferrand (FR); François Finck, Chatel-Guyon (FR); Dominique Guiet, Clermont-Ferrand (FR)

(73) Assignee: Michelin Recherche Et Technique S.A., Granges-Paccot (CH)

( * ) Notice: Subject to any disclaimer, the term of this patent is extended or adjusted under 35 U.S.C. 154(b) by 362 days.

(21) Appl. No.: 11/305,170

(22) Filed: Dec. 19, 2005

(65) Prior Publication Data
US 2006/0156790 A1    Jul. 20, 2006

Related U.S. Application Data

(63) Continuation of application No. PCT/EP2004/006331, filed on Jun. 11, 2004.

(30) Foreign Application Priority Data
Jun. 18, 2003    (FR) .................................. 03 07374

(51) Int. Cl.
*G01M 17/02* (2006.01)
(52) U.S. Cl. .......................... 702/34; 702/41; 702/188; 73/7; 73/8; 73/9; 73/146; 701/36
(58) Field of Classification Search .................. 702/34, 702/41; 73/7–9, 146; 152/154
See application file for complete search history.

(56) References Cited

U.S. PATENT DOCUMENTS

| 6,212,947 B1 * | 4/2001 | Shimizu et al. ............... 73/146 |
| 2004/0158414 A1 | 8/2004 | Bertrand |
| 2004/0250613 A1 | 12/2004 | Robert et al. |
| 2005/0016649 A1 | 1/2005 | Poulbot et al. |
| 2005/0044943 A1 | 3/2005 | Godeau et al. |
| 2005/0061069 A1 | 3/2005 | Robert |

FOREIGN PATENT DOCUMENTS

| FR | 2 816 402 | 5/2002 |
| JP | 2003-050190 | 2/2003 |

* cited by examiner

*Primary Examiner*—Tung S Iau
*Assistant Examiner*—Sujoy K Kundu
(74) *Attorney, Agent, or Firm*—Buchanan Ingersoll & Rooney PC (57) ABSTRACT

A technique for predicting the wear of at least one tire whose tread has pattern elements and which is fitted to a terrestrial motor vehicle, and a system for implementing the technique that enables a user, such as the vehicle's driver, to know reliably at any given moment the level of wear on the tire or on all the tires, or how long the residual wear will last, or even the remaining available running distance. Also, the piloting of drive-aid systems such as "ABS" (anti-block braking system) or "ESP" (electric programmed stability device) systems can be adapted as a function of the wear characteristics of the vehicle.

56 Claims, 1 Drawing Sheet

Fig. 1

METHOD FOR PREDICTING THE WEAR OF A TIRE AND SYSTEM FOR IMPLEMENTING IT

BACKGROUND

This is a continuation of Application No. PCT/EP2004/006331, filed on Jun. 11, 2004, designating the U.S.

The present invention concerns a method for predicting the wear of at least one tire fitted to a terrestrial motor vehicle, and a wear prediction system for implementing the method. The invention is applicable to any type of automobile vehicle, whether a passenger car, heavy vehicle or construction machinery, and to any two-wheeled vehicle of the motorcycle type.

It is known to predict the wear of a tire fitted to an automobile vehicle by taking into account at the same time the way the vehicle is used during driving (i.e. how 'hard' it is driven), the specific characteristics of the vehicle and those of the tire, from the article "Evaluation of Tire Wear Performance, Olivier Le Maître, Manfred Süssner, Cesar Zarak—Society of Automotive Engineers (SAE) Technical Paper Series 980256, pp. 46-47 (International Congress and Exposition, Detroit, Mich., Feb. 23-26, 1998)".

To estimate how hard the vehicle is driven, the longitudinal and transverse accelerations at the vehicle's centre of gravity are measured at each wheel rotation (or as a function of time), and the sum of the acceleration information obtained is then stored in a matrix.

This acceleration information is used to obtain information representative of the forces and attitudes at the wheel centers of the vehicle's mounted assemblies (such as the longitudinal forces $F_x$, transverse forces $F_y$ and vertical forces $F_z$, the slip and camber angles for each tire and for a combination of transverse and longitudinal accelerations), using a "vehicle" model which takes account of the static adjustments of toe-in and camber, the vehicle's static load conditions, the properties of tire-related forces and torques, and the toe-in and camber variations (due to rolling, pitching, conformity to transverse and longitudinal forces, and the self-alignment couple).

A "tire" model or tire wear model is then used to predict the wear from given conditions applied to the wheel centers (as a function of $F_x$, $F_y$, $F_z$ and the slip and camber angles for a given tire).

This wear model takes into account the mechanical specifications of the tire's functions (rigidities of the tread, crown and sidewalls) based on finite element results and on experimental data, and enables the prediction of the local distribution of stresses and the slippage rate in the contact area, from which the tread wear can be predicted.

A purpose of the invention is to propose a new method for predicting the wear of at least one tire whose tread has pattern elements and which is fitted to a terrestrial motor vehicle, and a prediction system for implementing the said method that enables a user, such as the vehicle's driver, to know reliably at any given moment the level of wear on the tire or on all the tires (or how long the residual wear will last or even the residual kilometer running distance that results therefrom), and/or to adapt the piloting of drive-aid systems such as "ABS" (anti-block braking system) or "ESP" (electric programmed stability device) systems as a function of the wear characteristics of the vehicle.

SUMMARY OF THE INVENTION

To that end the wear prediction method according to the invention comprises the following successive stages:
(i) wheel characteristics relating to at least one wheel, which include the forces applied at the wheel centre in the longitudinal, transverse and vertical directions and the camber γ and slip δ angles, are obtained for each revolution of the wheel or at given time intervals,
(ii) the said wheel characteristics are treated in relation to parameters that characterize the tire mounted on the said wheel to obtain, for each wheel revolution or for the said given time intervals, contact characteristics of the said tread patterns that characterize the contact area of the tire with the ground on which it is rolling, which represent forces applied on each tread pattern in the said longitudinal, transverse and vertical directions, and
(iii) the contact characteristics are treated for the prediction of the instantaneous wear characteristics that represent the wear of each tread pattern at each rotation of the wheel or at the given time intervals, and these instantaneous characteristics are summed over a given period to obtain the predicted cumulative wear characteristics for each tread pattern, the method according to the invention being such that it also comprises the following successive stages:
(iv) the measurement at a given instant of at least one actual cumulative wear characteristic of the tire on at least one of the tread pattern elements, or averaged over an axial section of the tire,
(v) comparison of at least one of the said predicted cumulative characteristics obtained in stage (iii) with the corresponding actual characteristic measured in stage (iv), and
(vi) assessment of the result of the comparison carried out in stage (v) for the implementation of a new cycle of corrected instantaneous and cumulative wear characteristics.

Advantageously, before the said stage (i) the method comprises:
measurement, in real time and for each wheel revolution or at given time intervals, of rolling parameters applied at the vehicle's centre of gravity during rolling, which include the intensities of the longitudinal $\gamma_x$ and transverse $\gamma_y$ accelerations or the corresponding longitudinal and transverse forces $F_x$ and $F_y$ (these accelerations or forces being measured by accelerometers or dynamometers, or being obtained from "ABS" or "ESP" systems or even from a "GPS" global positioning system), and then
a treatment of these accelerations or forces measured for each wheel revolution or at the said given time intervals in relation to parameters that characterize the vehicle, to obtain the characteristics envisaged in stage (i) for each wheel revolution or at the said given time intervals.

Note that the said wheel characteristics can be obtained directly by measuring the three components of the resultant of forces exerted by the ground surface over which the vehicle is rolling on the tire's contact area, which is determined by treatment of at least two measurements of the circumferential extension or contraction in at least one sidewall of the tire at two points fixed in space, located at different azimuths along the circumference. This circumferential sidewall contraction or extension is advantageously estimated by measuring the distance between the cords of the carcass ply in the sidewalls. Reference can be made to patent specification WO-A-03/014693 (corresponding to U.S. Published Application No. 2005/0158414) in the name of the present applicants for a detailed description of this measurement of wheel characteristics from the forces in the contact area.

According to another characteristic of the invention, the said rolling parameters also comprise the vehicle's speed V, again measured at the centre of gravity, and/or the load carried by the vehicle. Preferably these rolling parameters comprise this speed V and the load carried, in combination.

According to another characteristic of the invention, the method comprises the measurement in real time of static adjustments that include the toe-in and camber, before the said stage (iii).

According to another characteristic of the invention, the treatment envisaged in the said stage (iii) is also a function of parameters relating to the rolling ground surface, such as whether it is dry, wet or damp (determined for example by whether the windscreen wipers have been actuated) and/or the temperature of the said rolling surface, for the prediction of the said instantaneous wear characteristics.

In one embodiment of the invention the said actual cumulative wear characteristics envisaged in the said stage (iv) are obtained by examining the tire when the vehicle is at rest (this examination being simply visual or carried out using a suitable measuring device such as a "depth meter" or a laser beam).

In a first variant of this embodiment, the said actual cumulative wear characteristics envisaged in stage (iv) are obtained using means for the continuous or discontinuous measurement of the tire wear, provided on the vehicle and designed to inform the vehicle's driver, in real time, when at least one of the said tread pattern elements has reached one or more predetermined wear thresholds.

In a first example embodiment of this first variant according to the invention, the said stage (iv) consists in using the wear measurement means described in international patent application PCT/EP02/10936 (corresponding to U.S. Published Application No. 2005/0016649) in the name of the present applicants. The said stage (iv) then consists in measuring the electric capacitance or resistance within the said tread pattern element and deducing therefrom the height of the tread pattern from a relationship that relates the said capacitance or resistance to the height, for example by providing within the tire an electronic acquisition module connected to the said tread pattern element underneath the latter.

This capacitance or resistance value can be measured by a module for the acquisition of these values, provided within the tire. This can also be effected by a pattern-related capacitance measurement, by determining the tuning frequency of a passive resonance circuit comprising at least one condenser formed by the tread pattern element and an inductance connected to the condenser in the tire tread, by means of an interrogation circuit mounted on the wheel or on a fixed part of the vehicle adjacent to the wheel.

In the first of the above cases a pattern-related capacitance measurement can be carried out by tele-energisation of the acquisition module via an interrogation circuit mounted on the wheel or on a fixed part of the vehicle adjacent to the wheel, and transmitting to the interrogation circuit the capacitance measurement acquired by the module via an inductance coupled to the acquisition module in the tire.

In a second example embodiment of the first variant according to the invention, the said stage (iv) consists in using the wear measurement means described in international patent application PCT/EP02/12262 (corresponding to U.S. Published Application No. 2004/0250613) in the name of the present applicants. That application describes a method for measuring the wear of a tire whose tread pattern elements are interconnected by grooves, the vehicle comprising a chassis and a suspension system that provides a flexible connection between the chassis and the wheel, the said stage (iv) then consisting in the following:

a) at a given instant, measuring a value that represents the distance between, on the one hand, a first point on the said suspension system opposite the tire and occupying a position or a plurality of positions such that the orthogonal projection of the said first point on the circumferential median plane of the tire remains an equal distance from that of the axis of the wheel on the said plane, or a second point on the chassis opposite the tire and, on the other hand, the top surface of at least one of the said tread pattern elements opposite the said first or second point, b) either, in a first case, measuring at the said given instant a reference value that represents a distance measured between the said first or second point and the bottom of one of the said grooves opposite the said first or second point, or, in a second case, subsequently measuring another reference value that represents a distance between the said first point and one of the said top surfaces, and c) comparing the value measured in paragraph a) with the reference value measured in paragraph b) in order to deduce, in the said first case a wear datum representing the height of the said tread pattern by differential measurement at the said instant, and in the said second case a wear datum representing the evolution of the wear of the top of the said pattern within a given time interval.

According to a third example embodiment of the first variant according to the invention, the said stage (iv) consists in using the measurement means described in international patent application PCT/EP03/00888 (corresponding to U.S. Published Application No. 2005/0061069) in the name of the present applicants. The said stage (iv) then comprises the allocation, to a discrete impedance variable representing the impedance of a passive tuned circuit contained in at least one of the tread pattern elements, of a discrete wear variable representing the wear of the tread pattern.

Advantageously, the said stage (iv) then comprises measurement of the resonance frequencies of the tuned circuit which respectively represent values of the impedance variable, and a comparison of each frequency measured with one or more reference resonance frequencies each representing a tread pattern wear below at least one of the thresholds. Preferably, the tuned circuit comprises a coil and n ($n \geq 1$) condenser(s) mounted across the terminals of the coil.

In a fourth example embodiment of this first variant according to the invention, the said stage (iv) consists in using the wear measurement means described in international patent application PCT/EP03/00557 (corresponding to U.S. Published Application No. 2005/0044943) in the name of the present applicants. The said stage (iv) then comprises the allocation, to an energy variable representing the energy of an electromagnetic radiation such as the visible light transmitted from the space outside the said tire to the space inside it through at least one of the said tread pattern elements, of a wear variable representing the wear of the said pattern element(s). According to another characteristic of this stage (iv), the said energy variable itself represents the exposure of a means for the transmission of electromagnetic radiations on the top surface of the said pattern element.

The tire for implementing this stage (iv) then has within its body at least one electromagnetic radiation transmission means, provided for the transmission through at least one of the said tread pattern elements of an incident ray coming from the space outside the tire into its inside space, from the moment when this transmission means is exposed at the top surface of the said pattern element.

Preferably, the transmission means or each of them are permeable to visible light (i.e. translucent or transparent) and can consist for example of rubber(s) or of one or more optical fiber(s).

According to a second variant embodiment of the invention, the said actual cumulative wear characteristics envisaged in the said stage (iv) are obtained via measurement means provided on the vehicle for measuring the average wear of the said tread pattern elements over an axial section of the tire.

Advantageously, according to this second variant the said stage (iv) consists, successively, in the following:

estimation of the value $R_{e,\,t}$ of the rolling radius of the tire at an instant t, comparison of this estimated value $R_{e,\,t}$ with at least one reference value $R_{e,\,t0}$ for the rolling radius that corresponds to a given degree of wear of the same tire at a previous time $t_0$, and calculation of the ratio $R_{e,\,t}/R_{e,\,t0}$, deduction from this ratio $R_{e,\,t}/R_{e,\,t0}$ of the average wear ratio over an axial section of the tire, which is equal to the average height $h_t$ of the tread pattern elements at time t to their average height $h_{t0}$ at the time $t_0$, via a wear law specific to the said tire.

According to another characteristic of this second variant, the said value $R_{e,\,t}$ of the tire's rolling radius at time t is estimated by:

measuring at a given time t the number of rotations of the wheel on which the tire is mounted since the said earlier time $t_0$, measuring at the time t the distance traveled by the vehicle since the earlier time $t_0$, obtaining a theoretical value $R_{th,\,t}$ of the rolling radius at the time t from the ratio of the said distance traveled to the said number of wheel rotations at time t, determination at time t of corrective parameters related to the vehicle's rolling conditions, in particular including the temperature and internal pressure of the tire, the load and the drive or braking torque applied to the tire, and calculating the said estimated value $R_{e,\,t}$ of the tire's rolling radius at the said time t from the said theoretical value $R_{th,\,t}$ and from the said corrective parameters.

In an embodiment of the invention, the said prediction method is such that its stage (vi) comprises an initialization of the said or each predicted cumulative characteristic obtained in stage (iii) for the next prediction cycle, taking into account the difference between the value of the said or each predicted cumulative characteristic and that of the corresponding actual cumulative wear characteristic measured in stage (iv).

According to another embodiment of the invention, the prediction method is such that the said stage (vi) comprises an adaptive correction of the treatments envisaged in the said stages (ii) and (iii) during the next prediction cycle, taking into account the ratio between the said or each predicted cumulative characteristic obtained in stage (iii) and the corresponding actual cumulative wear characteristic measured in stage (iv).

Note that other, more complex initialization or "resetting" methods can also be used, for example ones which use the characteristic of wear rate over the last few kilometers traveled, for the correction of the predicted cumulative wear characteristic.

In general it should be noted that the said predicted instantaneous wear characteristics and/or the said cumulative wear characteristics obtained in stage (iii) represent one or more given circumferential axial zones of the tire tread concerned.

Note also that the prediction method according to the invention advantageously comprises the provision of information in real time to the vehicle's driver, about the wear either of all the tread pattern elements or of those among them which have sustained most wear.

Note that the prediction method according to the invention provides reliable knowledge, at a given instant, not only of the degree of wear of a tire but also of the residual use or the residual number of kilometers that can still be covered, as a result of that wear.

Note also that this prediction method according to the invention can be used to provide the predicted wear characteristics for piloting algorithms in the vehicle's safety system, these algorithms being provided for the control of drive-aid systems such as "ABS" or "ESP" systems, so as to adapt the piloting parameters of those systems.

A wear prediction system according to the invention for implementing the prediction method described above is such that it comprises essentially:

a RAM vehicle memory containing a database that relates to a plurality of terrestrial motor vehicles each having tires fitted on wheels, this database containing, for each vehicle, its mass, its geometrical characteristics and its slip rigidity characteristics, means for obtaining, for each wheel revolution or at given time intervals, wheel characteristics relating to at least one wheel that comprise the forces applied at the centre of the wheel in the longitudinal X, transverse Y and vertical Z directions and the camber $\gamma$ and slip $\delta$ angles, a RAM tire memory containing a database relating to a plurality of different tires, with information such as their sizes and the geometrical and mechanical characteristics of each of their tread patterns, a first treatment unit designed to treat the said wheel characteristics in relation to the tire parameters extracted from the said tire memory that characterize the tire fitted to the said wheel, and to deduce therefrom, for each wheel revolution or at the said given time intervals, contact characteristics of the said tread patterns that characterize the contact area of the said tire with the rolling surface that represent the forces applied on each pattern element in the directions X, Y and Z, a second treatment unit designed to predict, from the said contact characteristics, instantaneous wear characteristics that represent the wear of each tread pattern at each wheel revolution or at the given time intervals, and to accumulate these instantaneous characteristics over a given period, so as to obtain predicted cumulative wear characteristics for each pattern, and a resetting unit designed to integrate, at a given instant, at least one actual cumulative wear characteristic of the tire on at least one of the tread pattern elements or averaged over an axial section of the tire, in order to compare at least one of the said predicted cumulative wear characteristics with the corresponding actual wear characteristic and to take account of the result of that comparison with a view to carrying out a new prediction cycle of corrected instantaneous and cumulative wear characteristics, this actual cumulative wear characteristic being able to be obtained from measurement means that may or may not be fitted on the vehicle.

Advantageously, the said wear prediction system according to the invention also comprises:

measurement means designed to measure, in real time and for each wheel revolution or at the said given time intervals, the rolling parameters applied at the centre of gravity of the rolling vehicle, including the intensities of the longitudinal $\gamma_x$ and transverse $\gamma_y$ accelerations or the corresponding longitudinal and transverse forces $F_x$, and $F_y$, and a third treatment unit designed to treat the said accelerations or forces measured for each wheel revolution or at the said time intervals in relation to the said vehicle parameters, to obtain the said wheel characteristics for each wheel revolution or at the said intervals.

According to another characteristic of the invention, the said rolling parameters also include the speed V of the vehicle, again measured at its centre of gravity, and/or the load carried by the vehicle.

According to another characteristic of the invention, the said wear prediction system also comprises, upstream from the said second treatment unit, means for the measurement in real time of static adjustments including the toe-in and camber.

According to another characteristic of the invention, the said second treatment unit is designed to predict the said instantaneous wear characteristics as a function of parameters relating to the rolling ground surface, such as whether it is dry, wet or damp (determined for example by whether the windscreen wipers are actuated) and/or the temperature of the said surface.

According to an advantageous embodiment of the invention, the system comprises means for measuring the said actual cumulative wear characteristics, which are fitted on the vehicle and are designed to inform the vehicle's driver in real time when one or more predetermined wear thresholds have been reached on at least one of the said patterns.

In a first example of this embodiment referring to the international patent application PCT/EP02/10936 mentioned earlier, the said measurement means are designed to measure the electric capacitance or resistance within the said tread pattern element and to deduce therefrom the height of the tread pattern from a relationship that relates the said capacitance or resistance to the said height.

In a second example of this embodiment referring to the international patent application PCT/EP02/12262 mentioned earlier, in which the tire's tread pattern elements are interconnected by grooves and the vehicle comprises a chassis and a suspension system that provides a flexible connection between the chassis and the wheel, the said measurement means are designed to:

a) measure at a given instant a value that represents the distance between, on the one hand, a first point on the said suspension system opposite the tire and occupying a position or plurality of positions such that the orthogonal projection of the said first point on the circumferential median plane of the tire remains an equal distance from that of the wheel's axis on the said plane, or a second point on the chassis opposite the tire, and on the other hand, the top surface of at least one of the said pattern elements opposite the said first or second point, b) either, in a first case, measuring at the said given instant a reference value that represents a distance measured between the said first or second point and the bottom of one of the said grooves opposite the said first or second point, or, in a second case, subsequently measuring another reference value representing a distance measured between the said first point and one of the said top surfaces, and to c) compare the value measured in paragraph a) with the reference value measured in paragraph b) to deduce therefrom, in the first case, a wear datum representing the height of the tread pattern by differential measurement at the said instant, and in the second case a wear datum that represents the evolution of the wear of the top of the pattern over a given time interval.

In a third example of this embodiment referring to the international patent application PCT/EP03/00888 mentioned earlier, the said measurement means are designed to allocate, to a discrete impedance variable representing the impedance of a passive tuned circuit contained in at least one of the pattern elements, a discrete wear variable that represents the wear of the pattern.

In a fourth example of this embodiment referring to the international patent application PCT/EP03/00557 mentioned earlier, the said measurement means are designed to allocate a wear variable that represents the wear of the tread pattern(s) to an energy variable that represents the energy of an electromagnetic radiation such as visible light transmitted from the space outside the tire to its inside space through at least one of the said pattern element(s).

The said energy variable itself represents the exposure of a means for the transmission of electromagnetic radiations at the top surface of the said tread pattern element.

According to another advantageous embodiment of the invention, the said means for measuring the said actual cumulative wear characteristics are provided on the vehicle to measure the average wear of the said tread pattern elements over an axial section of the tire.

Advantageously, the said measurement means are designed to:

estimate the value $R_{e,t}$ of the rolling radius of the tire at a time t, and then compare this estimated value $R_{e,t}$ with at least one reference value $R_{e,t0}$ of the rolling radius that corresponds to a given degree of wear of the same tire at an earlier time $t_0$, calculating the ratio $R_{e,t}/R_{e,t0}$, and then deduce from this ratio $R_{e,t}/R_{e,t0}$ the average wear ratio over an axial section of the tire which equals the average height ht of the tread pattern elements at time t over their average height $h_{t0}$ at time $t_0$, via a wear relationship specific to the tire.

According to another characteristic of this other embodiment according to the invention, the said value $R_{e,t}$ of the tire's rolling radius at time t is estimated by:

first means, designed to measure at a time t the number of rotations of the wheel on which the tire is fitted, since the said earlier time $t_0$, second means, designed to measure at this time t the distance traveled by the vehicle since the said earlier time $t_0$, third means, designed to measure at the time t corrective parameters relating to the vehicle's rolling conditions, in particular including the temperature and internal pressure of the tire, the load, and the drive or braking torque applied to the tire, and an on-board computer designed to provide a theoretical value $R_{th,t}$ of the rolling radius at this time t from the ratio of distance traveled/number of wheel revolutions at time t, to calculate the said estimated value $R_{e,t}$ of the rolling radius at time t from the theoretical value $R_{th,t}$ and the corrective parameters, to calculate the ratio of this estimated value $R_{e,t}$ to the estimated value $R_{e,t0}$ of the rolling radius at the said time $t_0$, and to deduce therefrom the said average wear ratio.

Advantageously, the said first means comprise an "ABS" anti-block braking system associated with an "ESP" electronic programmed stability device.

Also in an advantageous way, the said second means are designed to measure the said distance traveled either directly via a reversing-aid radar, or indirectly via a "GPS" global positioning system, or from the actual vehicle speed/angular wheel velocity ratio. In the latter case, the said actual vehicle speed/angular wheel velocity ratio is advantageously given by the association of an anti-collision radar with an "ABS" anti-block braking system.

DESCRIPTION OF THE DRAWING

The aforesaid characteristics of the present invention and others will be better understood on reading the following description of an example embodiment of the invention, which is given for illustrative and non-limiting purposes and which relates to the attached drawing in which.

DESCRIPTION OF PREFERRED EMBODIMENTS

Figure 1:
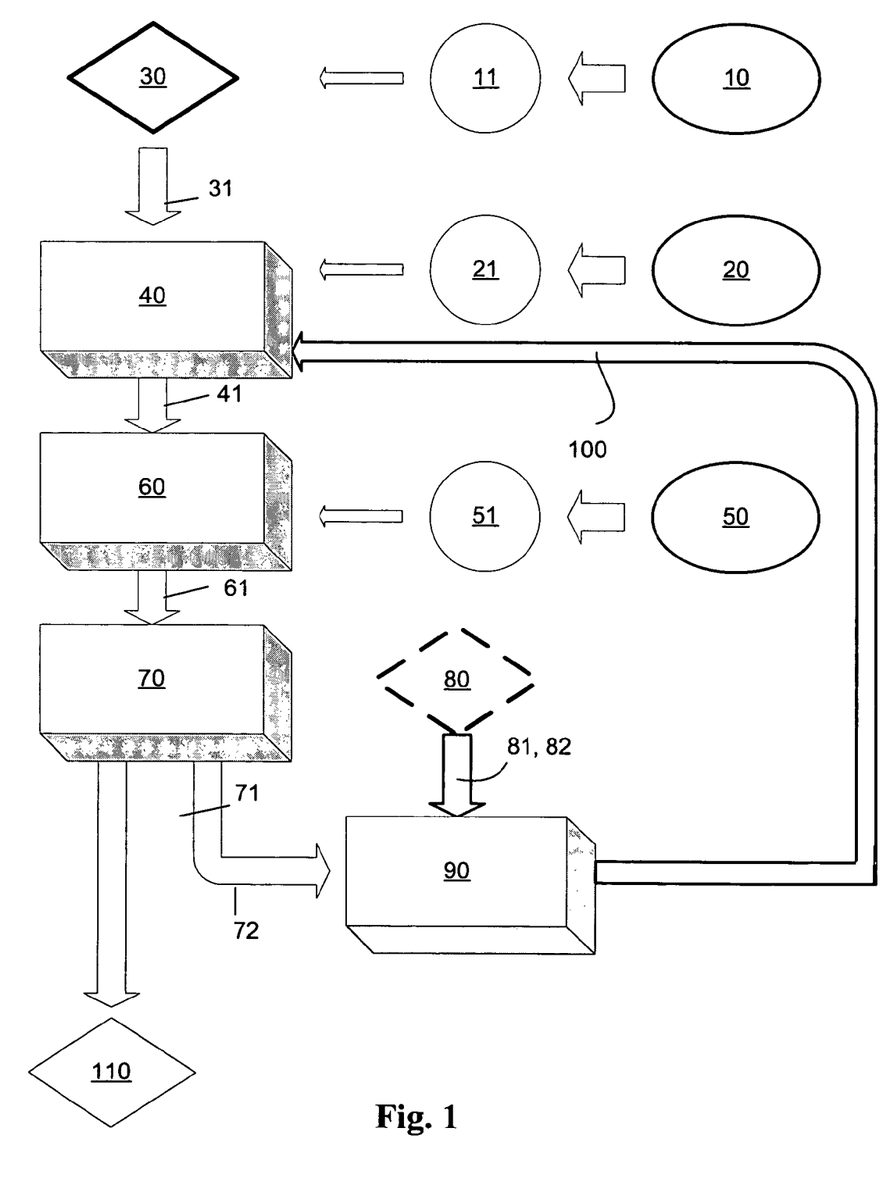
The single FIGURE is a block diagram illustrating the essential constituent elements, according to an example embodiment of the invention, of a system for predicting the wear of at least one tire fitted on a terrestrial motor vehicle, and the main stages of a wear prediction method implemented by this system.

As can be seen in the single FIGURE, a wear prediction system according to an example embodiment of the invention comprises essentially:

only optionally: a RAM route memory 10 containing a database relating to a plurality of routes for terrestrial motor vehicles, for example road or motorway circuits;

a RAM vehicle memory 20 containing a database relating to a plurality of terrestrial motor vehicles each having tires fitted on wheels, this database including in particular, for each vehicle, its mass, its geometrical characteristics (such as the height of its centre of gravity, its wheel base, its track, its initial toe-in and camber settings, the elastic-kinematic characterization of its suspension system), and its slip rigidity characteristics;

measurement means 30 designed to measure, in real time and for each wheel revolution or at given time intervals, rolling forces 31 applied at the centre of gravity of any of these vehicles during rolling (optionally from parameters 11 contained in the memory 10 that characterize one of the said routes that has been selected) and comprising in particular the intensities of the longitudinal $\gamma_x$ and transverse $\gamma_y$ accelerations or the corresponding forces $F_x$ and $F_y$, the speed V of the vehicle also measured at the centre of gravity and/or the load carried, or measurement means (not shown) designed to measure directly wheel characteristics 41 that include the forces applied at the wheel centre in the X, Y and Z directions and the camber $\gamma$ and slip $\delta$ angles;

only when the said measurement means 30 are used:

a treatment unit 40 designed to treat the rolling forces 31 measured for each wheel revolution or at the said given time intervals by the measurement means 30 in relation to parameters 21, extracted from the memory 20, that specifically characterize the vehicle selected, and to deduce therefrom the wheel characteristics 41 for each wheel rotation or at the said time intervals;

at least one RAM tire memory 50 containing a database relating to a plurality of different tires, with information such as their sizes and the geometrical and mechanical characteristics of each of their tread patterns i;

a treatment unit 60 designed to treat the wheel characteristics 41 in relation to parameters 51 extracted from the memory 50 that specifically characterize the tire fitted to the wheel, and to deduce therefrom, for each wheel revolution or at the given time intervals, characteristics 61 of their tread patterns i which characterize the contact area of the tire with the rolling ground surface that represent the forces applied to each pattern element i in the X, Y, and Z directions;

a treatment unit 70 designed to predict, from the said characteristics 61 of tread patterns i and if necessary from parameters related to the rolling ground surface such as whether it is dry or wet and/or the temperature of the said surface, instantaneous wear characteristics 71 that represent the wear of each pattern element i at each wheel rotation and to accumulate these predicted instantaneous wear characteristics 71 over a cycle of given period T, so as to provide the vehicle's driver with cumulative wear information 72 after the said rolling cycle predicted for each tread pattern element i (or at least for the pattern element i whose predicted wear is most severe);

optionally, means 80 fitted on the vehicle and designed to measure at a given instant the actual wear of each pattern element i (local wear) or the overall wear of the tire (i.e. averaged over an axial section of the tire), this local or overall wear being advantageously able to be measured continuously at each wheel revolution or discretely, for example cumulatively over the said period T, to provide actual wear values 81 or 82 (respectively instantaneous or cumulative), a resetting unit 90 designed to integrate the actual wear values 81 or 82, to compare the predicted wear values 72 with the corresponding actual wear values 82 and to modify the treatment of the rolling parameters 31 by the unit 40 during the next prediction cycle (see the arrow 100 representing this "initialization" of the treatment unit 40), and an on-board computer 110 installed in the passenger compartment of the vehicle, which is connected to the said treatment unit 70 and is designed to inform the vehicle's driver about the wear of at least one tire at a given instant, or about how much wear is still left or the number of kilometers that can still be driven as a result, and/or which is designed to provide the predicted wear characteristics for piloting algorithms in the vehicle's safety system, these algorithms being designed for the control of drive-aid systems such as "ABS" or "ESP" systems.

The memory 20 containing the database relating to vehicles comprises for example the following parameters 21 for each vehicle:

mass supported by the front axle (kg), mass supported by the rear axle (kg), type of transmission: traction or propulsion, wheel base: distance between front and rear axles: E in m, tracks (front/rear): distance between the left and right wheel centers: V1 and V2 in m, rigidities of the axles (front/rear): KZ1 and KZ2 in N/m, rigidities of the anti-roll bars (front/rear): C1 and C2 in Nm/rad, static wheel toe-in (front/rear): B10 and B20 in degrees, induced steering coefficient under vertical deflection (front/rear): B11/B21 in degrees/m, static cambers (front/rear): G10 and G20 in degrees,
induced camber coefficients due to vertical deflection (front/rear): G11, G21 (degrees/m),
induced camber coefficients due to roll (front/rear): GB1, GB2 (degrees/degrees),
heights of the centre of gravity and of the front/rear roll centers: HG, H01, H02 in m,
anti-plunge ratio (%),
anti-rear ratio (%),
braking distribution ratio: % of the total braking force taking place at the front axle,
running speed of the vehicle (V in km/h),
aerodynamics coefficient,
rolling resistance coefficient (%),
acceleration of gravity: 9.81 in $m/s^2$,
lever arm of the self-alignment couple: in m,
slip angle at zero thrust: $d_y0$ in degrees.

The measurement means 30 comprise accelerometers or dynamometers respectively designed to measure, for each wheel revolution or at given time intervals, the intensities of the longitudinal $\gamma_x$ and transverse $\gamma_y$ accelerations or the corresponding forces $F_x$ and $F_y$ applied at the centre of gravity of a given vehicle, these acceleration or force values being provided for example in the form of bi-histograms $\gamma_x/\gamma_y$ or $F_x/F_y$ (abscissa/ordinate) constructed at the spatial frequency of wheel revolutions or by integration over time. Note that the said accelerations or forces can also be obtained from "ABS", "ESP" or "GPS" systems.

As indicated earlier, it should be noted that the said measurement means 30 could be replaced by means designed to measure directly the wheel characteristics 41 (including the forces applied at the wheel centre in the X, Y and Z directions and the camber γ and slip δ angles) from measurement of the three components of the resultant of forces exerted by the rolling surface on the contact area of the tire, which is determined by the treatment of at least two measurements of circumferential extension or contraction in at least one sidewall of the tire at two points fixed in space located at different azimuths along the circumference. This circumferential contraction or extension of the sidewalls is advantageously estimated by measuring the distance between the cords of the carcass ply in the sidewalls. Reference can be made to patent specification WO-A-03/014693 in the name of the present applicants for a detailed description of this measurement of the wheel characteristics 41 from the forces in the contact area.

The optional treatment unit 40 is for example designed to treat this bi-histogram of accelerations and forces and to deduce from it, for each wheel revolution or at the said given time intervals, the forces applied at the wheel centre in the said X, Y and Z directions and the camber γ and slip δ angles (the speed V of the vehicle being input into the unit 40 as a constant, or not, depending on the route chosen). For the calculation of the forces applied at the wheel centre, the input data are the said accelerations $\gamma_x$ and $\gamma_y$, the static load of the vehicle and if necessary the speed and the steering-wheel angle, and in the first instance the forces applied at each axle are calculated.

First of all, from the overall load of the vehicle and its geometry the Z-forces for each axle are determined. Then, from the acceleration $\gamma_y$ and the vehicle's geometry, the Y-forces for each axle are determined.

Then, from the acceleration $\gamma_x$, the vehicle's geometry, the braking law and the drive ability distribution, the X-forces for each axle are calculated. In effect, the vehicle is subjected to an aerodynamic resistance force, to the rolling resistance of the front and rear axles, and to a drive or braking torque (the distribution of the latter force between the front and rear axles depending on the design of the vehicle and, in the case of braking, on the braking law that defines the front/rear distribution of the said force).

From the X-forces for each axle, the X-forces for each wheel are determined.

Then the Z-forces for each wheel are calculated by taking the longitudinal and transverse load transfers into account. In effect, the total vertical load on a wheel is the sum of the static load on the wheel (equal to half the load on the axle) and load variations respectively due to the longitudinal load transfers (pitch equilibrium) and the transverse load transfers (roll equilibrium).

From there, the Y-forces for each wheel are calculated by computing the sum of the induced steerings and cambers (induced by the roll and under vertical deflection), the slip of the rear wheels (calculation of the body slip and the Y-forces of the rear wheels) and the slip angles of the front wheels (calculation of the steering angle of the steering-wheel and the Y-forces of the front wheels).

The tire memory 50 containing the database of tires contains in particular parameters for each tire such as its inside diameter "on the seat", its outer diameter H, its axial width B and its ratio H/B, and the geometrical and mechanical characteristics of each tread pattern i including in particular the heights of rubber $h_i$, the grooving fraction (also known as the "empty fraction") of each tread pattern i in the contact area, and the rigidities $Rx_i$ and $Ry_i$ of the tread pattern i in the X and Y directions.

The treatment unit 60 is designed to treat the data on forces applied at the wheel centre and the camber and slip angles in relation to the said tire parameters 51 extracted from the memory 50, via a tire model or law, to deduce therefrom, for each wheel revolution or at the said given time intervals, the said pattern characteristics 61 in the contact area of the tire with the rolling ground surface, as for example:
the forces $f_{xi}$, $f_{yi}$, $f_{zi}$ on each tread pattern i in the directions X, Y, Z respectively, and
the length $L_i$ and width $l_i$ of each tread pattern i in the contact area.

Note that the aforesaid optional route memory 10 can serve to "reset" the treatment units 40 or 60, for example to take account of the specific nature of the rolling ground surface.

The treatment unit 70 is designed to predict, from the said characteristics 61 of the tread pattern elements i in the contact area and if necessary the more or less dry or wet condition of the rolling surface and its temperature, the said instantaneous wear characteristics 71 of each pattern element i representing the wear after each wheel revolution or at the given time intervals, on the basis of a wear model or law such as Archard's law which is well known to those familiar with the field (on this subject see the article J. F. ARCHARD, "Contact and rubbing of flat surfaces", J. Appl. Phys., 24 (1953) 981-988).

These wear characteristics 71, such as the absolute or relative height loss of each tread pattern element i or its wear rate, are in particular a function of the sliding length of each pattern element i in the contact area, the aforesaid forces $f_{xi}$, $f_{yi}$, $f_{zi}$ on each pattern element i, the abrasion of the material constituting each tread pattern i, and its length $L_i$ and width $l_i$.

Note that the treatment unit 70 can provide overall wear data or wear data discrete for zones of the tire (i.e. concerning the whole, or one or more zones of the tire, for example distributed over its axial width, such as the shoulders and/or one or more zones having as their plane of symmetry the median circumferential plane of the tire, or located on either side of that plane between the shoulders).

As indicated earlier, these wear data 72 predicted over a cycle of period T are obtained by acceleration over the number of revolutions in the cycle or by integration of the instantaneous data 71 over time. As indicated above, it should be noted that the said cumulative data 72 obtained can be overall, or discrete for zones of the tire.

The resetting unit 90 then compares the predicted data 72 with the wear data 82 previously integrated in the resetting unit and obtained directly:

either by a visual inspection when the vehicle is at rest, carried out for example by the driver or by an outside specialist, or, advantageously, via the said tire wear measurement means 80, continuously or discontinuously (when the vehicle is at rest and/or rolling), which are provided on the vehicle to inform the driver in real time when one or more predetermined wear thresholds have been reached, either on at least one pattern element i or averaged over an axial section of the tire.

When the system is designed to use actual cumulative wear values obtained by visual inspection or measurements independent of the vehicle, for example with a depth meter, it comprises means for simply receiving these values and integrating them in the memory. These means can comprise a connection point to which a unit with a keyboard can be attached for manual input. The system could also be connected directly to an external measurement unit via the said connection point.

As means 80 for the measurement of wear on at least one tread pattern element i of the tire (or all the pattern elements i), those described in the international patent applications mentioned earlier: PCT/EP02/10936, PCT/EP02/12262, PCT/EP03/00888 and PCT/EP03/00557, can be used with advantage.

As means 80 for measuring the average wear on an axial section of the tire, it is advantageous to use means designed to estimate the value $R_{e,t}$ of the tire's rolling radius at a time t, then comparing this estimated value $R_{e,t0}$ for the said rolling radius that corresponds to a degree of wear of the same tire determined at an earlier time $t_0$ (corresponding for example to zero wear of the tire) by calculating the ratio $R_{e,t}/R_{e,t0}$, and then deducing from that ratio $R_{e,t}/R_{e,t0}$ the average wear ratio on an axial section of the tire which is equal to the average height $h_t$ of the tread pattern elements at time t over their average height $h_{t0}$ at time $t_0$, by virtue of a wear law specific to the tire.

The said means 80 for measuring the rolling radius of the tire(s) comprise essentially, in a vehicle equipped therewith:

first means for measuring at a time t the number of rotations of the wheel(s) on which the tire(s) is/are fitted since a reference time $t_0$, these means advantageously comprising an ABS system associated with an ESP system, these two systems making it possible to obtain a measurement precision of the number of wheel rotations accurate to about 1/48 or 1/96 of a rotation;

second means for measuring at that time t the distance traveled by the vehicle since the time $t_0$, either directly by a reversing-aid radar (comprising ultrasound pickups in a known way), or indirectly by a GPS ("global positioning system"), or even from the ratio between the actual speed of the vehicle and the angular velocity of the wheel, which can be given by the association of an anti-collision radar with an ABS system;

third means for measuring at that time t corrective parameters that relate to the rolling conditions of the vehicle, the said third means comprising in particular means for determining the internal temperature and pressure of the tire, the load and the drive or braking torque applied to the tire;

an on-board computer designed to provide, for the tire or for each tire considered:

a theoretical value $R_{th,t}$ of the tire's rolling radius at time t, given by the ratio of the distance traveled to the number of wheel rotations, an estimated value $R_{e,t}$ (i.e. corrected) of the tire's rolling radius from the said theoretical value $R_{th,t}$ and the said corrective parameters, the ratio of this estimated value $R_{e,t}$ to the estimated value $R_{e,t0}$ of the same tire's rolling radius at the said reference time $t_0$, the overall wear ratio (i.e. averaged over the section of the tire) equal to the average height $h_t$ of the tread pattern elements at time t over their average height $h_{t0}$ at time $t_0$, from the said ratio $R_{e,t}/R_{e,t0}$ and by virtue of an empirical wear law specific to the tire.

Still with reference to the single FIGURE, during the following measurement cycle the resetting unit 90 then corrects the treatment by the unit 40 of the rolling parameters 31, for example by taking into account the difference or the existing quotient between the said predicted and measured values or by using the wear rate characteristic over the last few kilometers traveled, to correct the predicted cumulative wear characteristic so that a new cycle of predictions can be carried out (still for the tire as a whole or only for certain of its zones).

The on-board computer 110 informs the vehicle's driver continuously or on demand about the wear corresponding either to all the tread pattern elements or to that or those among them which are the most severely worn, or to that or those among them which are most severely worn on one or more zones of the tire in an axial section thereof. The said computer 110 can also inform the driver about how much wear is left or about the kilometers that can still be driven granted the existing wear, and/or adapt piloting parameters of drive-aid systems such as "ABS" or "ESP" systems.

The invention claimed is:

1. A method for predicting the wear of at least one tire whose tread comprises tread pattern elements defining a contact area of the tire with the ground, the at least one tire mounted on a wheel of a terrestrial motor vehicle, comprising the steps of:

A. operating the motor vehicle;

B. obtaining during predetermined durations, selected wheel characteristics, including:

B1. forces applied at the wheel center in the longitudinal, transverse, and vertical directions, respectively, of the vehicle, B2. camber angle γ, and B3. slip angle δ;

C. treating the selected wheel characteristics obtained in step B, in relation to parameters characterizing the tire, to obtain for each predetermined duration, contact characteristics of the tread pattern elements representing forces applied to each tread pattern element in the longitudinal, transverse, and vertical directions;

D. predicting, from the contact characteristics obtained in step C, instantaneous wear characteristics representing the wear of each tire pattern element for each of the predetermined durations, and summing the instantaneous characteristics over a given period to obtain a predicted cumulative wear characteristic for each tread pattern element;

E. measuring at least one actual cumulative wear characteristic of the tread at a given instant;

F. comparing the at least one actual cumulative wear characteristic from step E to a corresponding predicted cumulative wear characteristic from step D; and G. repeating steps A-F while correcting the treatment of the selected wheel characteristics in step C in accordance with the comparison made in step F.

2. The method according to claim 1, wherein the predetermined duration of step B is defined by one rotation of the at least one tire.

3. The method according to claim 1, wherein the predetermined duration of step B is defined by a given time interval.

4. The method according to claim 1, wherein step E comprises measuring at least one actual cumulative wear characteristic of at least one tread pattern element at a given instant.

5. The method according to claim 1, wherein step F comprises measuring at least one actual cumulative wear characteristic of the tread pattern elements, averaged across an axial section of the tire.

6. The method according to claim 1, further comprising, prior to step B, the steps of:
measuring in real time for each duration, at least one rolling parameter applied at the vehicle's center of gravity during rolling along a route, the parameters selected from among:
intensities of the longitudinal $\gamma_x$ and transverse $\gamma_y$ accelerations, and
longitudinal and transverse forces $F_x$ and $F_y$; and then treating the at least one measured parameter in relation to parameters characterizing the vehicle to obtain the wheel characteristics of step B.

7. The method according to claim 6, wherein the speed of the vehicle measured at its center of gravity is another of the rolling parameters from among which a selection is made.

8. The method according to claim 6, wherein the load defined by the vehicle is another of the rolling parameters from among which a selection is made.

9. The method according to claim 1, wherein the wheel characteristics are obtained directly during step B by measuring the three components of the resultant of forces exerted by the ground surface over which the vehicle is rolling on the tire's contact area, such measurement determined by treatment of at least two measurements of the circumferential extension or contraction in at least one sidewall of the tire at two points fixed in space, located at different azimuths along the tire's circumference.

10. The method according to claim 1, further comprising the measurement in real time of static adjustments that include the toe-in and camber, before step D.

11. The method according to claim 1, wherein the predicting of instantaneous wear characteristics in step D is performed as a function of conditions of the ground, including the type of ground and a degree of dryness thereof.

12. The method according to claim 1, wherein step F is performed with the tire at rest.

13. The method according to claim 1, wherein the actual cumulative wear characteristics are measured in step E continuously or discontinuously by means provided on the vehicle for informing the vehicle's driver, in real time, when at least one of the treat pattern elements has reached a predetermined wear threshold.

14. The method according to claim 13, wherein step E comprises measuring the electric capacitance or resistance within the tread pattern element and deducing therefrom a height of such tread pattern from a ratio of between the capacitance, or the resistance, to the height.

15. The method according to claim 13, wherein the tread pattern elements of the tire are interconnected by grooves, and the vehicle comprises a chassis and a suspension system that ensures a flexible connection between the chassis and the wheel, step E comprising:

E1. at a given instant, measuring a value which represents a distance between:
E1a. a first point lying on the suspension system opposite the tire and occupying a position or a plurality of positions such that the orthogonal projection of said first point on the circumferential median plane of the tire remains an equal distance from that of the axis of the wheel on said plane, or a second point lying on the chassis opposite the tire and,
E1b. the top surface of at least one of said tread pattern elements opposite said first or second point,
E2. measuring at said given instant a reference value that represents a distance between said first or second point and the bottom of one of said grooves opposite said first or second point, and
E3. comparing the value measured in E1a with the reference value measured in E1b in order to deduce a wear datum representing the height of said tread pattern by differential measurement at said instant.

16. The method according to claim 15, wherein step E further comprises allocating, to a discrete impedance variable representing the impedance of a passive tuned circuit contained in at least one of the tread pattern elements, a discrete wear variable representing the wear of the at least one tread pattern element.

17. The method according to claim 15, wherein step E further comprises allocating, to an energy variable representing the energy of an electromagnetic radiation such as the visible light transmitted from the space outside the tire to the space inside it through at least one of the tread pattern elements, a wear variable representing the wear of said at least one pattern element.

18. The method according to claim 17, wherein said energy variable itself corresponds to the exposure of a means for the transmission of electromagnetic radiation on the top surface of said at least one pattern element.

19. The method according to claim 13, wherein the tread pattern elements of the tire are interconnected by grooves, and the vehicle comprises a chassis and a suspension system that ensures a flexible connection between the chassis and the wheel, step F comprising:

E1. at a given instant, a value is measured which represents a distance between:
E1a. a first point on said suspension system opposite the tire and occupying a position or a plurality of positions such that the orthogonal projection of said first point on the circumferential median plane of the tire remains an equal distance from that of the axis of the wheel on said plane, or a second point lying on the chassis opposite the tire, and
E1b. the top surface of at least one of said tread pattern elements opposite said first or second point,
E2. measuring at said given instant a reference value that represents a distance between said first point and one of said top surfaces, and
E3. comparing the value measured in E1a with the reference value measured in E1b in order to deduce a wear datum representing the evolution of the wear of the top of said at least one tread pattern element within a given time interval.

20. The method according to claim 19, wherein step E further comprises allocating, to a discrete impedance variable representing the impedance of a passive tuned circuit contained in at least one of the tread pattern elements, a discrete wear variable representing the wear of the at least one tread pattern element.

21. The method according to claim 19, wherein step E further comprises allocating, to an energy variable representing the energy of an electromagnetic radiation such as the visible light transmitted from the space outside the tire to the space inside it through at least one of the tread pattern elements, a wear variable representing the wear of said at least one pattern element.

22. The method according to claim 21, wherein said energy variable itself corresponds to the exposure of a means for the transmission of electromagnetic radiation on the top surface of said at least one pattern element.

23. The method according to claim 1, wherein the actual cumulative wear characteristics are measured in step E by measurement means provided on the vehicle for measuring the average wear of said tread pattern elements over an axial section of the tire.

24. The method according to claim 23, wherein step E further comprises the following successively formed steps:
estimating the value $R_{e,t}$ of the rolling radius of the tire at an instant t,
comparing the estimated value $R_{e,t}$ with at least one reference value $R_{e,t0}$ for the rolling radius that corresponds to a given degree of wear of the same tire at a previous time $t_0$, and calculation of the ratio $R_{e,t}/R_{e,t0}$ and
deducing, from the calculated ratio $R_{e,t}/R_{e,t0}$ the average wear ratio over an axial section of the tire, which is equal to the average height ht of the tread pattern elements at time t to their average height ht0 at the time t0, via a wear law specific to said tire.

25. The method according to claim 24, wherein said value Ret of the tire's rolling radius at time t is estimated by:
measuring at a given time t the number of rotations of the wheel on which the tire is mounted since said earlier time to,
measuring at the given time the distance travelled by the vehicle since the earlier time to,
obtaining a theoretical value $R_{th,t}$ of the rolling radius at the given time t from the ratio of said distance travelled to said number of wheel rotations at the given time t,
determining, at time t, corrective parameters related to the vehicle's roiling conditions, including the temperature and internal pressure of the tire, the load and the drive or braking torque applied to the tire, and
calculating said estimated value $R_{e,t}$ of the tire's rolling radius at said time t from said theoretical value $R_{th,t}$ and from said corrective parameters.

26. The method according to claim 1, wherein step E comprises an initialization of each predicted cumulative characteristic obtained in step D for the next prediction cycle, in accordance with the difference between the value of each predicted cumulative characteristic and that of the corresponding actual cumulative wear characteristic measured in step F.

27. The method according to claim 1, wherein the correction made in step G is in accordance with the ratio of each predicted cumulative characteristic obtained in step D to the corresponding actual cumulative wear characteristic measured in step E.

28. The method according to claim 1, wherein the correction in step G is made in accordance with the wear rate of the tire during a predetermined number of kilometres most recently travelled by the vehicle.

29. The method according to claim 1, further comprising the step of providing in real time to the vehicle's driver, information about tread wear.

30. A wear prediction system operable during operation of a terrestrial motor vehicle for predicting the wear of at least one tire mounted on a wheel of said terrestrial motor vehicle and which tire comprises tread pattern elements defining a contact area of the tire with the ground, the system, comprising:
a RAM vehicle memory containing a database that relates to a plurality of terrestrial motor vehicles each having tires fitted on wheels, this database containing, for each vehicle, its mass, its geometrical characteristics and its slip rigidity characteristics,
means for obtaining, during predetermined durations, wheel characteristics relating to at least one wheel, including the forces applied at the center of the wheel in the longitudinal, transverse, and vertical directions, and the camber $\gamma$ and slip angle $\delta$,
a RAM tire memory containing a database relating to a plurality of different tires, with information including their sizes and the geometrical and mechanical characteristics of their tread pattern elements, and,
a first treatment unit for treating said wheel characteristics in relation to the parameters extracted from said tire memory that characterize the tire and to deduce therefrom, for each predetermined duration, contact characteristics of the tread pattern elements which represent the forces applied on each tread pattern element in the longitudinal, transverse, and vertical directions,
a second treatment unit for predicting from said contact characteristics, instantaneous wear characteristics that represent the wear of each tread pattern element for each of the predetermined durations, and to accumulate these instantaneous characteristics over a given period, to obtain predicted cumulative wear characteristics for each tread pattern element, and
a resetting unit for integrating, at a given instant, at least one actual cumulative wear characteristic of the tire on at least one of the tread pattern elements or averaged over an axial section of the tire, in order to compare at least one of said predicted cumulative wear characteristics with the corresponding actual wear characteristic for carrying out a Previously Presented prediction cycle of corrected instantaneous and cumulative wear characteristics.

31. The system according to claim 30, further comprising:
measurement means for measuring, in real time and for each predetermined duration, rolling parameters applied at the center of gravity of the rolling vehicle, the parameters selected from among: the intensities of the longitudinal $\gamma_x$ and transverse $\gamma_y$, accelerations and the corresponding longitudinal and transverse forces $F_x$ and $F_y$, and
a third treatment unit for treating said accelerations or forces measured for each predetermined duration in relation to said vehicle parameters, to obtain said wheel characteristics for each predetermined duration.

32. The system according to claim 31, wherein said rolling parameters are also selected from among the speed V of the vehicle measured at the vehicle's center of gravity, and the load carried by the vehicle.

33. The system according to claim 30 further comprising means for the direct measurement of said wheel characteristics by measuring the resultant forces exerted by the ground surface on the tire's contact area in each of the longitudinal, transverse and vertical directions, the measurement determined on the basis of a plurality of measurements of circumferential extension or contraction of a tire sidewall at the two points fixed in space and located at different azimuths along the tire's circumference.

34. The system according to claim 30 further comprising upstream from said second treatment unit, means for the measurement in real time of static adjustments, including the toe-in and camber.

35. The system according to claim 30 wherein said second treatment unit is operable to predict the instantaneous wear characteristics as a function of parameters relating to the rolling ground surface, selected from among the surface's degree of dryness and temperature.

36. The system according to claim 30 further comprising measurement means fitted on the vehicle for measuring the at least actual cumulative wear characteristic and informing the vehicle's driver in real time when one or more predetermined wear thresholds have been reached on at least one of said tread pattern elements.

37. The system according to claim 36 wherein said measurement means is operable to measure electric capacitance or resistance within said at least one tread pattern element and to deduce therefrom a height of the at least one tread pattern from a relationship that relates said capacitance, or resistance, to said height.

38. The system according to claim 36, wherein the tire's tread pattern elements are separated by grooves, said vehicle comprising a chassis and a suspension system producing a flexible connection between the chassis and the wheel, said measurement means being operable to:
a) measure, at a given instant, a value representing a distance between:
  a point lying on said suspension system opposite the tire and occupying a position such that an orthogonal projection of said point on the circumferential median plane of the tire remains an equal distance from an orthogonal projection of the axis of the wheel on said plane, and
  the top surface of at least one of said tread pattern elements opposite said point,
b) measure at said given instant a reference value that represents a distance measured between said point and the bottom of one of said grooves opposite said point,
c) compare the value measured in paragraph 1) with the reference value measured in paragraph b) to deduce a wear datum representing the height of said tread pattern by differential measurement at said instant.

39. The system according to claim 17, wherein the tire's tread pattern elements are separated by grooves, said vehicle comprising a chassis and a suspension system producing a flexible connection between the chassis and the wheel, said measurement means being operable to:
a) measure, at a given instant, a value representing a distance between:
  a point located on the chassis opposite the tire, and
  the top surface of at least one of said tread pattern elements opposite said point,
b) measure at said given instant a reference value that represents a distance measured between said point and the bottom of one of said grooves opposite said point, and
c) compare the value measured in paragraph a) with the reference value measured in paragraph b) in order to deduce a wear datum representing the height of said tread pattern by differential measurement at said instant.

40. The system according to claim 36, wherein the tires tread pattern elements are separated by grooves, said vehicle comprising a chassis and a suspension system producing a flexible connection between the chassis and the wheel, said measurement means being operable to:
a) measure, at a given instant, a value representative of a distance between:
  a point lying on said suspension system opposite the tire and occupying a position, such that an orthogonal projection of said point on the circumferential median plane of the tire remains at an equal distance from an orthogonal projection of the axis of the wheel on said plane, and
  the top surface of at least one of said tread pattern elements opposite said point,
b) measure a reference value that represents a distance between said point and one of said top surfaces, and
c) compare the value measured in paragraph a) with the reference value measured in paragraph b) in order to deduce a wear datum representing the evolution of the wear of the top of said pattern with a given time interval.

41. The system according to claim 36, wherein said measurement means is operable to allocate, to a discrete impedance variable representing the impedance of a passive tuned circuit contained in at least one of the tread pattern elements, a discrete wear variable representing the wear of the at least one tread pattern element.

42. The system according to claim 36, wherein said measurement means is operable to allocate, to an energy variable representing the energy of an electromagnetic radiation such as the visible light transmitted from the space outside said tire to the space inside it through at least one of said tread pattern elements, a wear variable representing the wear of said at one tread pattern element.

43. The system according to claim 42, wherein said energy value corresponds to the exposure of a means for the transmission of electromagnetic radiations on the top surface of said at least one tread pattern element.

44. The system according to claim 30, wherein said measurement means is operable for measuring an average wear of said tread pattern elements over an axial section of the tire.

45. The system according to claim 44, wherein said measurement means is operable to:
estimate the value $R_{e,t}$ the rolling radius of the tire at an instant t, and then
compare this estimated value $R_{e,t}$ with at lest one reference value $R_{e,t0}$ for the rolling radius that corresponds to a given degree of wear of the same tire at a previous time $t_0$, and calculation of the ratio $R_{e,t}/R_{e,t0}$, and
deduce from this ratio $R_{e,t}/R_{e,t0}$ the average wear ratio over an axial section of the tire, which is equal to the average height $h_t$ of the tread pattern elements at time t over the average height $h_{t0}$ at the time $t_0$, via a wear law specific to said tire.

46. The system according to claim 45, wherein said measurement means comprises, for estimating said value $R_{e,t}$:
first means for measuring at instant t the number of rotations of the wheel on which the tire is mounted since said earlier time $t_0$,
second means for measuring at the instant t a distance travelled by the vehicle since the earlier time $t_0$,
third means for measuring at said instant t corrective parameters related to the vehicle's rolling conditions, including the temperature and internal pressure of the tire, the load and the drive or braking torque applied to the tire, and
an on-board computer for providing a theoretical value $R_{th,t}$ of the rolling radius at the instant t from the ratio of: distance travelled to the number of wheel rotations at the instant t, to calculate said estimated value $R_{e,t}$ the tire's rolling radius at said instant t from said theoretical value $R_{th,t}$ and from the corrective parameters, to calculate the ratio of: this estimated value $R_{e,t}$ the estimated value $R_{e,t0}$ the rolling radius at said time $t_0$, and to deduce therefrom said average wear ratio.

47. The system according to claim 46, wherein said first means comprises an anti-block system associated with an electronic programmed stability device.

48. The system according to claim 46, wherein said second means is operable to measure said distance travelled directly by means of a reversing-aid radar.

49. The system according to claim 46, wherein said second means is operable to measure said distance travelled indirectly via a global positioning system.

50. The system according to claim 46, wherein said second means is operable to measure said distance travelled, from the ratio of: actual vehicle speed to angular velocity of the wheel.

51. The system according to claim 50, wherein said ratio is provided by the association of an anti-collision radar with an anti-block braking system.

52. The system according to claim 47, wherein said second means is operable to measure said distance travelled directly by means of a reversing-aid radar.

53. The system according to claim 47, wherein said second means is operable to measure said distance travelled indirectly via a global positioning system.

54. The system according to claim 47, wherein said second means is operable to measure said distance travelled, from the ratio of: actual vehicle speed to angular velocity of the wheel.

55. The system according to claim 54, wherein said ratio is provided by the association of an anti-collision radar with an anti-block braking system.

56. The method according to claim 1, wherein the performing of steps B-G occurs on the vehicle as it is operated in driving step A, and further comprising, during step A, providing to a driver of the vehicle, information related to the predicted cumulative wear characteristics of the at least one tire.

\* \* \* \* \*